(12) United States Patent
Gerber (10) Patent No.: US 10,076,602 B2
(45) Date of Patent: Sep. 18, 2018

(54) NASAL DOUCHE WITH VALVE THAT CAN BE ACTUATED BY RESPIRATORY AIR

(71) Applicant: Benedict Gerber, Bottighofen (CH)

(72) Inventor: Benedict Gerber, Bottighofen (CH)

( * ) Notice: Subject to any disclaimer, the term of this patent is extended or adjusted under 35 U.S.C. 154(b) by 122 days.

(21) Appl. No.: 15/034,771

(22) PCT Filed: Sep. 6, 2014

(86) PCT No.: PCT/EP2014/002423
§ 371 (c)(1),
(2) Date: May 5, 2016

(87) PCT Pub. No.: WO2015/067332
PCT Pub. Date: May 14, 2015

(65) Prior Publication Data
US 2016/0263307 A1    Sep. 15, 2016

(30) Foreign Application Priority Data
Nov. 5, 2013 (EP) .................................... 13005214

(51) Int. Cl.
*A61M 31/00* (2006.01)
*A61M 5/00* (2006.01)
(Continued)

(52) U.S. Cl.
CPC ........... *A61M 3/0279* (2013.01); *A61H 35/04* (2013.01); *A61M 3/0241* (2013.01);
(Continued)

(58) Field of Classification Search
CPC ............ A61H 35/04; A61H 2201/0153; A61H 2201/0192; A61H 2201/5025;
(Continued)

(56) References Cited

U.S. PATENT DOCUMENTS 6,715,485 B1 * 4/2004 Djupesland ......... A61M 3/0279
128/203.12
D530,815 S    10/2006 Murphy et al.
(Continued)

FOREIGN PATENT DOCUMENTS

| EP | 2 036 527 A1 | 3/2009 |
| EP | 1 747 771 B1 | 4/2010 |
| KR | 2011-0056462 A | 5/2011 |

OTHER PUBLICATIONS

Dec. 12, 2014 Search Report issued in International Patent Application No. PCT/EP2014/002423.
(Continued)

*Primary Examiner* — Jason Flick
(74) *Attorney, Agent, or Firm* — Oliff PLC (57) ABSTRACT

A nasal douche having a valve, container part and cap part, wherein the container part serves to receive irrigation liquid and carries cap part. The cap part has a nose attachment with an outlet opening for irrigation liquid connected fluidically to interior of container part via discharge channel, wherein nose attachment is intended to be attached to a nostril of the user. The container part or cap part is assigned a mouthpiece for controlling the valve, wherein the valve is closed in a rest position and flow of irrigation liquid out through the nose attachment is thus suppressed, and wherein the valve can be brought to an open position, under the action of respiratory air when the user blows into the mouthpiece, and irrigation liquid thus flows out through the nose attachment, wherein respiratory air or ambient air flows into the container part to allow the outward flow.

15 Claims, 5 Drawing Sheets

(51) Int. Cl.
*A61M 3/02* (2006.01)
*A61H 35/04* (2006.01)
*B05B 9/08* (2006.01)
*F16K 31/126* (2006.01)
*F16K 3/26* (2006.01)
*B05B 1/30* (2006.01)
*B05B 11/00* (2006.01)

(52) U.S. Cl.
CPC ............ *B05B 9/0811* (2013.01); *F16K 3/265* (2013.01); *F16K 31/1262* (2013.01); *A61H 2201/0153* (2013.01); *A61H 2201/0192* (2013.01); *A61H 2201/5025* (2013.01); *A61M 2205/076* (2013.01); *A61M 2210/0618* (2013.01); *B05B 1/3026* (2013.01); *B05B 11/0094* (2013.01)

(58) Field of Classification Search
CPC .......... A61M 3/0279; A61M 2205/076; A61M 2210/0618; A61M 3/0241; B05B 11/0094; B05B 1/3026; B05B 9/0811; F16K 31/1262; F16K 3/265
USPC ....................................................... 604/275
See application file for complete search history.

(56) References Cited

U.S. PATENT DOCUMENTS

| | | | |
|---|---|---|---|
| 7,165,549 B2 | 1/2007 | Philipps et al. | |
| 7,377,901 B2 | 5/2008 | Djupesland et al. | |
| 7,481,218 B2 | 1/2009 | Djupesland | |
| 7,784,460 B2 | 8/2010 | Djupesland et al. | |
| 7,854,227 B2 | 12/2010 | Djupesland | |
| 7,934,503 B2 | 5/2011 | Djupesland et al. | |
| 8,146,589 B2 | 4/2012 | Djupesland | |
| 8,171,929 B2 | 5/2012 | Djupesland et al. | |
| 8,550,073 B2 | 10/2013 | Djupesland | |
| 8,590,530 B2 | 11/2013 | Djupesland et al. | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,205,209 B2 | 12/2015 | Djupesland | |
| 9,272,104 B2 | 3/2016 | Djupesland | |
| D759,805 S | 6/2016 | Djupesland | |
| 2009/0304802 A1 | 12/2009 | Djupesland et al. | |
| 2010/0035805 A1 | 2/2010 | Hafner | |
| 2010/0161140 A1* | 6/2010 | Doglioni Majer | A47J 31/405 700/283 |
| 2011/0023869 A1 | 2/2011 | Djupesland | |
| 2011/0053827 A1 | 3/2011 | Hafner | |
| 2011/0318345 A1 | 12/2011 | Djupesland | |
| 2014/0018295 A1 | 1/2014 | Djupesland | |
| 2014/0073562 A1 | 3/2014 | Djupesland | |
| 2014/0144442 A1 | 5/2014 | Djupesland et al. | |
| 2015/0013670 A1 | 1/2015 | Djupesland et al. | |
| 2015/0013677 A1 | 1/2015 | Djupesland et al. | |
| 2015/0053201 A1 | 2/2015 | Djupesland et al. | |
| 2015/0246194 A1 | 9/2015 | Djupesland et al. | |

OTHER PUBLICATIONS

Dec. 12, 2014 Written Opinion issued in International Patent Application No. PCT/EP2014/002423.

* cited by examiner

NASAL DOUCHE WITH VALVE THAT CAN BE ACTUATED BY RESPIRATORY AIR

The present invention relates to a nasal douche according to the preamble of patent claim 1.

KR 2011 0056462 A has disclosed a nasal douche which has a container portion with an irrigation liquid and a pipe portion with a Venturi pipe portion for spraying the irrigation liquid. The main body of the pipe portion is bent in a C-shaped manner and the Venturi pipe portion is formed thereon in a T-shaped manner at the central lower end of the C-shaped pipe portion. A negative pressure is generated when a user blows air into one end of the Venturi pipe portion, as a result of which the irrigation liquid is suctioned out of the container portion and transported in the direction of the nostril of the user via the pipe portion in order to irrigate the nose of the user with the irrigation liquid.

Document EP 2 036 527 A1 discloses a nasal douche with an elastic container for receiving irrigation liquid, wherein the container has an irrigation opening and a ventilation opening sealable by a finger. The ventilation opening is provided with a check valve which is open during use in the case of a pressure-free container and allows an emergence of irrigation liquid from the irrigation opening. By quickly pressing together the container, it is possible to close the check valve, as a result of which an emergence of irrigation liquid under pressure is possible from the irrigation opening.

A disadvantage of the known nasal douche is that, after filling the elastic container with irrigation liquid, the nasal douche always needs to be held in the hand during use since the irrigation liquid would otherwise leak continuously from the irrigation opening due to the open ventilation opening; this is accompanied by a very inexpedient use of the known nasal douche. The only control system to interrupt the drainage during use in the known nasal douche lies in the manual sealing of the ventilation opening with the finger, as a result of which the drainage is stopped, but a controlled drainage of the irrigation liquid from the container of the nasal douche is not possible in this manner.

Moreover, the known nasal douche usually has the further disadvantage that the irrigation liquid, which enters through a nostril of the nose of the user, does not only reemerge from the other nostril but can also drain into the oropharyngeal cavity due to the connection between the nasal cavity and the oropharyngeal cavity, which may have swallowing of the irrigation liquid as a consequence. However, this is not desirable since the irrigation liquid generally only serves to irrigate the nasal cavity of the user. Moreover, the irrigation liquid may also trigger, for example, unwanted nausea of the user during the use of the known nasal douche.

Furthermore, a passive transfer or active aspiration of the irrigation liquid into the larynx and the lower airways is also possible with the known nasal douche, wherein this may be perceived as uncomfortable by the user or this may even be dangerous for the user under certain circumstances.

It is therefore an object of the present invention to develop the known nasal douche in such a way that it is easier to handle the latter, controlled drainage of the irrigation liquid out of the container is made possible and, moreover, the drainage of irrigation liquid into the oropharyngeal cavity is prevented.

According to the invention, this object is achieved by a nasal douche having the features of patent claim 1.

The nasal douche in accordance with patent claim 1 has a valve, a container part and a cap part, wherein the container part serves to receive irrigation liquid and carries the cap part. The cap part has a nose attachment with an outlet opening for the irrigation liquid flow-connected to an interior of the container part via a discharge channel, the nose attachment being intended for attachment to a nostril of the user.

According to the invention, a mouthpiece for controlling the valve is assigned to the container part or the cap part, wherein the valve is closed in a rest position and this prevents the drainage of irrigation liquid through the nose attachment. By actuating the valve with respiratory air, the valve can be brought into an open position when the user blows respiratory air into the mouthpiece and irrigation liquid flows out through the nose attachment as a result thereof, with respiratory air or ambient air flowing into the container part for drainage.

A substantial advantage of the present invention is the actuation of the valve with respiratory air via the mouthpiece assigned to the container part or the cap part in order to bring the valve into the open position. In this manner, it is possible to introduce either respiratory air or ambient air into the container part, as a result of which a pressure difference is generated in the container part. As a result of this effect, a controlled drainage of the irrigation liquid from the container part of the nasal douche according to the invention is advantageously ensured in a manner dependent on the respiratory pressure blown therein.

Therefore, in contrast to the known nasal douche, a controlled drainage of the irrigation liquid from the container part is possible without manual actuation, and so the free available hand significantly simplifies the handling of the nasal douche according to the invention for the user. Only one hand needs to be used to hold the cap part and the respiratory air blown into the mouthpiece in a controlled manner allows the drainage of the irrigation liquid from the container part in the direction of the outlet opening of the nose attachment with a controlled flow rate.

Compared to the known nasal douche, the unrestricted use of container parts for the irrigation liquid, whether these have elastic or rigid properties, is likewise advantageous. On account of the controlled blowing-in of the respiratory air through the mouthpiece, the irrigation liquid can drain from the container part in the direction of the outlet opening with a greater or else with a lower respiratory pressure, depending on the desired flow rate. However, in so doing, there is no need to press the container part together, as is the case in the known nasal douche, in order to generate a higher pressure in the interior of the container.

A further substantial advantage in the present invention is the functional effect of blowing respiratory air into the mouthpiece. Since the user surrounds the mouthpiece in a sealing manner with his lips when blowing the respiratory air into the mouthpiece during use of the nasal douche according to the invention, a pressure increase is caused in the oral cavity as a result of active exhaling. In particular, this is carried out by virtue of the soft palate, which is a muscle plate, involuntarily sealing the nasal cavity, as a result of which, firstly, pressure is transferred to the mouthpiece and volumes disposed downstream thereof and, secondly, the irrigation liquid guided into a nostril through the nose attachment due to pressure is necessarily guided around the rear edge of the nasal septum in the nasal pharynx and channeled-off again by way of the opposite nostril. Consequently, crossing of the irrigation liquid into the airways lying below the palate is precluded and, accordingly, swallowing, ingress into the lower airways or aspiration is no longer possible compared to the known nasal douche.

Preferably, the container part is embodied as an independent component and the cap part is embodied as an independent component and these are fastened to one another, preferably in a separable manner. An advantage thereof is that the container part can be filled with irrigation liquid when the cap part is separated.

Further preferably, the cap part and the container part are fastened to one another by means of a screw-in connection or a bayonet closure. This allows a very simple and separable connection, without damaging the container part or the cap part in the process. Moreover, the container part of the nasal douche can be refilled with the irrigation liquid without problems.

In the case of the screw-in connection as a fastening between the independent cap part and the independent container part, it is advantageous if the screw-in connection is embodied in such a way that there already is a secure connection after little screwing between the independent cap part and the independent container part and, at the same time, a uniquely defined position of the independent cap part is adjustable in relation to the independent container part. This is advantageous, in particular, if the independent container part has an embodiment which is plane-symmetric or asymmetric in relation to an axis and accordingly needs to be aligned in front of the face of the user as soon as the nose attachment assigned to the cap part faces the user.

In the case of an independent cap part, the latter preferably has a shell-like shape and it serves for improved stability in the case of the connection with the container part. In this way, it is moreover possible for a portion of the container part to be encompassed by the shell-like shape. By way of suitable shaping of the cap part, good access to the valve member for the purposes of a simplified replacement of the same is ensured, depending on requirements.

Preferably, the independent cap part can be stored vertically in an unscrewed state, with the nose attachment being situated in the air and correspondingly being protected from contaminants, and the discharge channel of the nose attachment has an angle away from the horizontal such that residual emptying of the discharge channel and ventilation can take place spontaneously during storage.

Likewise, it is also conceivable that the independent cap part and the independent container part are fastened to one another by means of a force fit.

It is also possible that the container part has an integral embodiment with the cap part. This allows a compact design of the nasal douche according to the invention with ergonomic properties for the application.

Further preferably, the container part has a refill opening, which is sealable by means of a lid. The lid is preferably arranged on the side of the nasal douche distant from the cap part in order to simplify filling of the container part with irrigation liquid.

Preferably, the valve, in the rest position, seals a blown-in air channel leading from the mouthpiece to the container part, as a result of which no respiratory air or ambient air reaches the container part and the drainage of irrigation liquid from the container part in the direction of the outlet opening is prevented, and the valve can be brought into an open position when actuated with respiratory air such that the respiratory air reaches the container part via the blown-in air channel or ambient air reaches the container part and the irrigation liquid can drain from the container part in the direction of the outlet opening. In this arrangement of the valve, a defined amount of air can be introduced into the container part by controlled blowing-in of the respiratory air through the mouthpiece so as to control the flow rate of the irrigation liquid from the container part.

In the case where the valve is in contact with the irrigation liquid, i.e. the valve is situated in the interior of the container part or introduced into the outer wall of the container part, the task of the valve consists of preventing irrigation liquid from being able to flow back to the mouthpiece from the container part by way of the blown-in air channel. Consequently, the hydrostatic pressure of the irrigation liquid works against the ambient pressure and, when the valve is actuated with respiratory air, it is initially necessary to overcome the closing force of the valve before respiratory air can reach the container part. The valve only returns into its rest position when no respiratory air is blown into the container part anymore by way of the mouthpiece such that the access of the irrigation liquid to the mouthpiece and to the outlet opening is sealed again.

Alternatively, it is also conceivable for the valve to be arranged in an inlet channel between the surroundings and the irrigation liquid such that the valve can be brought into the open position when the valve is actuated with respiratory air and in the process opens up the flow path from the surroundings into the interior of the container part, as a result of which ambient air can reach the container part and, there, enables drainage of the irrigation liquid from the interior of the container part in the direction of the outlet opening of the nose attachment.

It is also conceivable for a pilot valve to be arranged in the blown-in air channel between the mouthpiece and the valve in the interior of the container part, said pilot valve being controlled by means of respiratory air, and for the pilot valve in turn to control the valve in the interior of the container part.

Preferably, the valve has a valve seat, which is preferably ring-shaped and preferably formed on the cap part, and a preferably plate-shaped valve member interacting therewith. At this point, it is mentioned that this valve is a specific solution to preclude the ingress of irrigation liquid from the container part into the blown-in air channel, with other technical solutions naturally also being able to come into question.

Further preferably, a web has a head which is preferably thickened at least approximately in an ovoid or spherical manner, wherein the valve member abuts on the valve seat, preferably under pretension, and it is embodied in a membrane-like, elastically deformable manner. The valve member preferably has a through hole at a central location, it can be pulled over the head with the through hole during assembly and it engages behind the head in the assembled state. Since the valve member is membrane-like and elastically deformable, it is possible to replace the valve member quickly and in a simple manner. This is advantageous, particularly for reasons of hygiene.

The head keeps the through hole of the assembled valve member in position and the radially outer edge of the plate-shaped valve member lifts from the valve seat when the closing force is overcome in order to allow the respiratory air to enter into the interior of the container part. This process causes a pressure change in the container part, as a result of which the drainage of the irrigation liquid from the container part in the direction of the outlet opening is made possible.

Since the valve member abuts on the valve seat, preferably under pretension, and the valve member only lifts from the valve seat once the closing force is exceeded when the respiratory air is blown into the mouthpiece, the valve member, on account of the pretensioned restoring force, very quickly returns into the closed rest position when the blowing of respiratory air into the mouthpiece is interrupted. This ensures that no irrigation liquid can reach the mouthpiece from the container part by way of the blown-in air channel in the rest position.

Preferably, the mouthpiece has an elastic material or is produced from same such that different distances between mouth and nose of the user are compensable during the application or by bending the mouthpiece.

Preferably, the mouthpiece is interchangeable and preferably available with different dimensions for physiognomically different user groups.

Preferably, the mouthpiece is insertable in an interchangeable manner into a receptacle of the cap part or pluggable onto an attachment of the cap part, wherein the mouthpiece preferably has a straight or angled embodiment.

In a further embodiment of the present invention, the valve seals the discharge channel in the rest position and opens up the discharge channel in the open position. By applying pressure with respiratory air from the mouthpiece, the valve can be brought into the open position in order to enable the controlled drainage of the irrigation liquid from the container part.

Preferably, the valve has a passage across the discharge channel as a valve seat, which interacts with a valve member, which is embodied as a closure pin and interacts with an actuation organ, in such a way that the closure pin seals the discharge channel in the rest position and the actuation organ displaces the closure pin in the open position when actuated by respiratory air in such a way that the aperture opens up the discharge channel.

Preferably, the container part has a ventilation opening and it is preferably provided with a check valve which prevents the emergence of irrigation liquid from the container part through the ventilation opening and admits the inflow of ambient air through the ventilation opening into the container part.

Preferably, the cap part can have a valve as described above in order to ensure the blowing-in of respiratory air into the container part and a further valve can serve to open up an aperture in a closure pin to the discharge channel of the nose attachment by means of an actuation organ. Accordingly, the mouthpiece preferably has a branch which, firstly, enables the blowing-in of the respiratory air into the container part and, simultaneously, enables the blowing-in of respiratory air to the actuation organ.

Preferably, the effect of the valve is also obtainable by way of a balloon arranged in the container part, wherein the respiratory air in the blown-in air channel inflates the balloon when applying respiratory air by blowing into the mouthpiece in such a way that said balloon displaces the irrigation liquid in the container part in such a way that the irrigation liquid can drain from the container part in the direction of the outlet opening of the nose attachment.

In a further embodiment, it is conceivable that the nose attachment does not have an integral embodiment with the cap part but instead the nose attachment is an independent, straight component which is mounted in a manner displaceable along the longitudinal direction thereof in a blind hole-shaped receptacle. The receptacle is formed by the cap part and an appendage integrally formed thereon. The discharge channel has on the inside transversely radial first apertures through the nose attachment, which first apertures are connected to the discharge channel, and it furthermore has transversely radial second apertures, which are separate from the discharge channel. A spring acting between the appendage and the nose attachment pushes the nose attachment into a rest position, wherein the first and second apertures are sealed by the cap part, and, in an open position, the second apertures on the one hand open up the connection channel and, on the other hand, the flow connection between the interior of the container part and the discharge channel of the nose attachment is established for the first apertures.

Further advantages and properties of the nasal douche according to the invention emerge from the following description of exemplary embodiments, which are explained on the basis of the drawing.

In a purely schematic manner.

Figure 1:
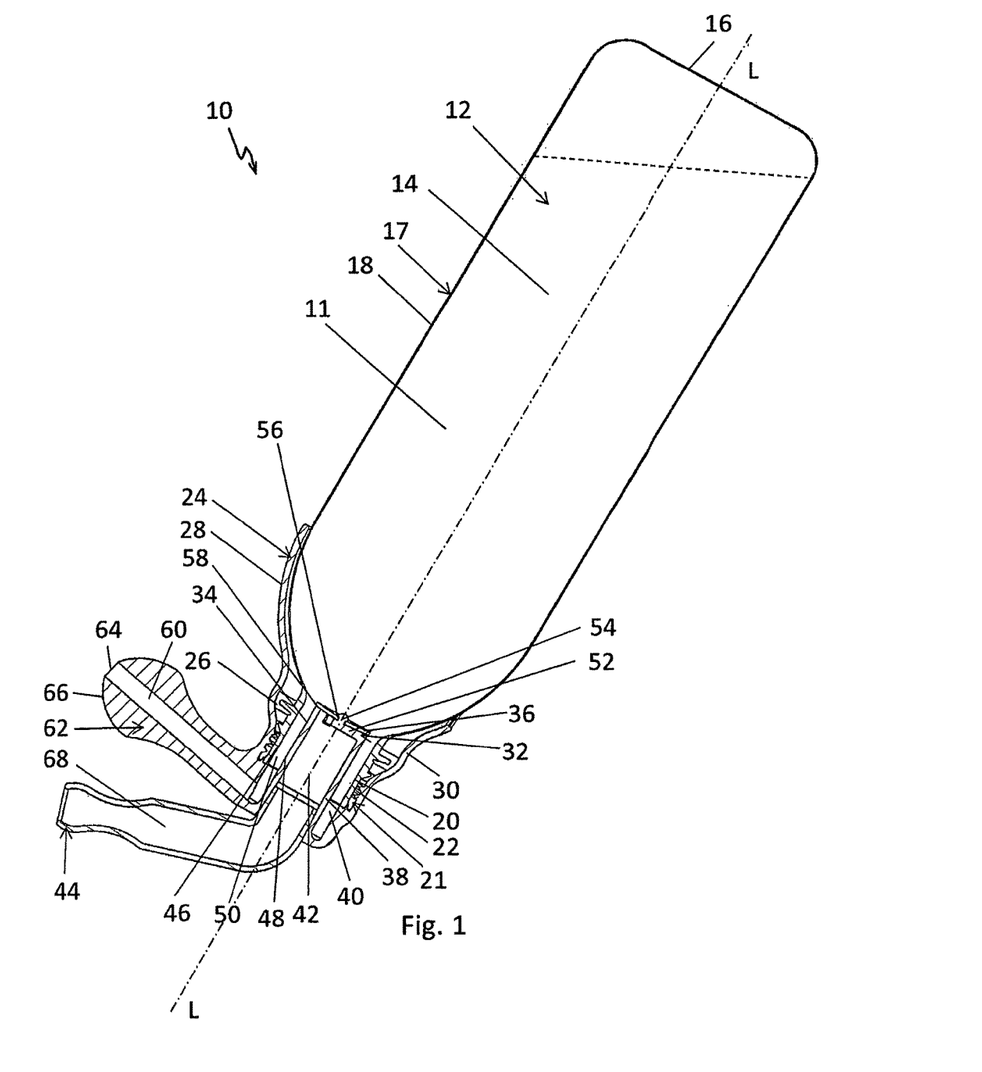
FIG. 1 shows a longitudinal section of a nasal douche according to the invention, comprising an independent container part for receiving irrigation liquid, an independent cap part, screwed onto the container part, comprising a nose attachment and an assigned mouthpiece, and a valve which, in the rest position, prevents the drainage of irrigation liquid through the mouthpiece.

A first exemplary embodiment in accordance with a nasal douche 10 according to the invention, shown in FIG. 1, is shown in the use position (overhead position), i.e. tilted by 180°.

In the interior 11 of an independent container part 12, the nasal douche 10 has an irrigation liquid 14 and it carries an independent cap part 24. In this exemplary embodiment, the container part 12 and the cap part 24 are independent components, which are fastened to one another in a separable manner by means of a screw-in connection 21.

Depending on application, the container part 12 can have, for example, a capacity of approximately 100 ml to approximately 500 ml and it is, for example, a bottle 12' with a bottle base 16 and a tapering bottleneck 20 adjoining a body of the bottle 18.

The maximum capacity of the container part 12 depends on, inter alia, the practice-oriented manageability of the nasal douche 10 according to the invention, i.e. the capacity should not be so great that the user is only still able to hold the nasal douche 10 in one hand with difficulty.

The container part 12 can be a well-known bottle or any type of container part 12 which is able to receive the irrigation liquid 14 in the interior 11 thereof.

A male thread 22 is attached to the outer side of the bottleneck 20 for the screw-in connection 21 between the cap part 24 and the container part 12.

The container part 12 can be produced from both a hard material and an elastic material. The material properties of the container part 12 do not have any influence on the functionality of the nasal douche 10 according to the invention. This is in contrast to the known nasal douche in which, as explained in the introduction, the container must have an elastic embodiment in order to generate a higher pressure by manual compression of the container.

For the screw-in connection 21, the independent cap part 24 is provided with a female thread 26 and, in accordance with FIG. 1, it is shown screwed onto the male thread 22 of the container part 12.

In this context, it is mentioned that it is also possible for the cap part 24 to have a female thread which is incompatible with conventional bottles, such as e.g. PET bottles, and so a specific container part with a corresponding male thread should be used in the nasal douche.

As an independent cap part 24, the latter preferably has a shell-like portion 28 and it serves in the assembled state as a mechanical support for the container part 12 in the region of the transition from the body of the bottle 18 to the tapered bottleneck 20. The shell-like portion 28 in this case has an integral embodiment with the cap part 24.

Preferably, at least one deep cutout 30 is introduced into the shell-like portion 28, said cutout allowing the user of the nasal douche 10 to service a valve 32 for reasons of hygiene.

The valve 32 has a ring-shaped valve seat 34 formed onto the cap part 24 and a plate-shaped valve member 36 interacting therewith.

The ring-shaped valve seat 34 is formed by the free end of an inverted section 38, coaxial with the longitudinal axis L coinciding with the container axis, of the cap part 24 in the aperture opening 40 of the bottleneck 20. The inverted section 38 has a hollow cylindrical shape and forms a receptacle 42 for a tube-like, angled mouthpiece 44. A pipe-shaped passage 50 for the irrigation liquid 14 emerges between the outer side 46 of the hollow cylindrical inverted section 38 and the inner side 48 of the hollow cylindrical bottleneck 20.

The inverted section 38 of the cap part 24 is open toward the bottle base 16 and it forms the ring-shaped valve seat 34. Adjacent to the valve seat 34 the inverted section 38 has a radially inward web 52 with a spherically thickened head 54 arranged centrally in relation to the valve seat 34. The valve member 36 has a membrane-like and elastically deformable embodiment and a through hole 56 at a central location.

When assembling the valve 32, the valve member 36 can be pulled over the head 54 with the through hole 56 and, in the assembled state, the elastically embodied valve member 36 engages behind the head 54. In so doing, the valve member 36 abuts on the valve seat 34 under pretension since the undercut in respect of the valve seat 34 is recessed. In the rest state of the valve member 36, i.e. in the case of a closed valve 32, the discharge of irrigation liquid 14 is prevented.

At the end 58, facing away from the bottle base 16, of the passage 50 for the irrigation liquid 14 which is closed there in the axial direction, a discharge channel 60 of a nose attachment 62 connects an outlet opening 64 to the passage 50 from the side. In the present exemplary embodiment, the nose attachment 62 is formed integrally onto the cap part 24 and projects laterally, with the discharge channel 60 of the nose attachment 62 and the ring-shaped passage 50 for the irrigation liquid 14 being flow-connected.

The discharge channel 60 of the nose attachment 62 ends at the end-side outlet opening 64 of the nose attachment 62, wherein the discharge channel 60 in the present exemplary embodiment is arranged angled in the direction of the bottle base 16 such that the angle between the longitudinal axis L and the longitudinal adjustment of the nose attachment 62 is less than 90°.

In this context, it should be mentioned that the discharge channel 60 could also be arranged parallel to the bottle base 16 and hence at right angles to the longitudinal axis L of the container part 12.

It is also conceivable, but not shown, that the container part 12 has an asymmetric or plane-symmetric embodiment in relation to the longitudinal axis L such that the discharge channel 60 could be arranged at an obtuse angle in relation to the longitudinal axis L of the container part 12.

Figure 2:
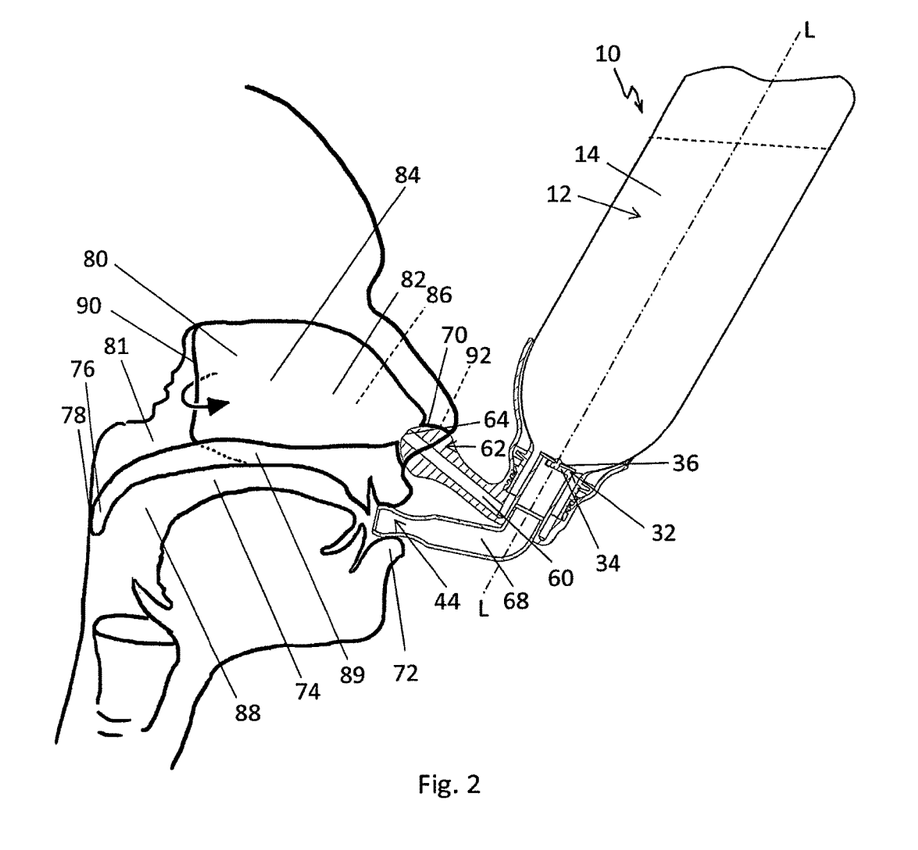
FIG. 2 shows a longitudinal section of the nasal douche according to the invention in accordance with FIG. 1, in an overview with a longitudinal section of the nasal pharyngeal cavity of a user.

A nose-side end region 66 of the nose attachment 62 has an olive-shaped thickened embodiment and it is suitable for placement against a nostril of the user (see FIG. 2). In this context, it should be mentioned that the nose-side end region 66 can have different shapes depending on the anatomical form of the nostril of the user in order to enable an ideal seat of the nose-side end region 66 of the nose attachment 62 on the nose of the user. In so doing, what should be taken into account, inter alia, is that no irrigation liquid 14 should emerge during use of the nasal douche 10 between the nostril of the user and the nose-side end region 66 of the nose attachment 62 and a sufficient seal should accordingly be ensured.

The nose attachment 62 is preferably assembled in a rigid manner in relation to the container part 12 in order to enable proper irrigation of the nose and, in the process, prevent slippage of the nose-side end region 66 of the nose attachment 62 in the nose.

In the present exemplary embodiment, the mouthpiece 44 is inserted in a rotatable manner in the hollow cylinder-shaped receptacle 42.

The mouthpiece 44 is intended to be taken into the mouth by the user in order to blow respiratory air into the container part 12 for irrigating the nose, wherein the valve 32 can be brought from the rest position into an open position in which the valve member 36 is lifted from the valve seat 34.

The mouthpiece 44 has an elastic material such that different distances between mouth and nose of the user are compensable during the application by bending the mouthpiece 44.

In the present exemplary embodiment, the mouthpiece 44 has an angled embodiment. However, it is also conceivable for the mouthpiece 44 to have a straight embodiment. In this case, the receptacle 42 for the mouthpiece 44 extends approximately radially.

If the nasal douche 10 according to the invention is filled with irrigation liquid 14 and, as shown in FIG. 1, sealed by the cap part 24 and tilted by 180° (i.e. if it is in an overhead position), the hydrostatic pressure of the irrigation liquid 14 acts on the plate-shaped valve member 36 of the valve 32, and so no irrigation liquid 14 can reach a blown-in air channel 68 of the mouthpiece 44 from the container part 12. As a result of the narrowed bottleneck 20 and the narrowed hollow cylinder-shaped passage 50 over the discharge channel 60 to the outlet opening 64, no ambient air can reach the container from the outside via the nose attachment 62, and so the irrigation liquid 14 cannot reach the outlet opening from the container part 12. In order to let the irrigation liquid 14 drain from the container part 12, a pressure difference must be caused in the container part 12.

How this is carried out according to the invention is explained in detail below in conjunction with FIG. 2.

When placing the nose attachment 62 of the nasal douche 10 according to the invention on a first nostril 70 of the user and surrounding the mouthpiece 44 of the nasal douche 10 according to the invention with the lips 72 of the user and blowing respiratory air into the mouthpiece 44, there is a pressure increase in the blown-in air channel 68 of the mouthpiece 44 as a result of the respiratory air.

Since the plate-shaped valve member 36 blocks the path of the respiratory air into the container part 12, the applied respiratory pressure must first overcome the closing force of the valve member 36. In other words, the respiratory air pressure needs to be greater than the sum of the closing force of the valve member 36 itself plus the hydrostatic pressure of the irrigation liquid 14 so that the valve member 36 can be lifted from the valve seat 34 in order to bring respiratory air into the container part 12 and thus generate a pressure difference in the container part 12.

A further effect becomes important in the present invention during the pressure increase of the respiratory air in the blown-in air channel 68 of the mouthpiece 44. As a precondition for the pressure increase, the soft palate 76 of the user rests tightly against a pharyngeal rear wall 78 and thus separates a nasal cavity 80 from an oropharyngeal cavity 88. The nasal cavity 80 is formed by a left nasal chamber 82 and a right nasal chamber 86, wherein these are spatially separated from one another by a nasal septum 84 and transition into a common nasopharyngeal cavity 81 behind the nasal septum 84. To the bottom, the nasal chambers 82, 86 are delimited by a hard palate 89 and the nasopharyngeal cavity 81 is delimited by the soft palate 76.

Consequently, the irrigation liquid 14 from the nasal douche 10 according to the invention can only drain through the nasal cavity 80 and the other nostril 92 when blowing the respiratory air into the container part 12 through the mouthpiece 44 and it cannot reach below into the oropharyngeal cavity 88 like in known nasal douches.

Accordingly, when the valve 32 is actuated with respiratory air from the mouthpiece 44 and when the closing force of the valve member 36 of the container part 12 is overcome, the irrigation liquid 14 flows through the passage 50 and the discharge channel 60 to the outlet opening 64 of the nose attachment 62 and, from there, into the left nasal chamber 86 (in this case) via the left nostril 92 (in this case), from there to the rear edge 90 of the nasal septum 84 and then, in the reverse flow direction, through the right nasal chamber 82 (in this case) to the right nostril 70 (in this case), where the irrigation liquid 14 then reemerges. Swallowing the irrigation liquid 14 is therefore no longer possible with the nasal douche 10 according to the invention since the soft palate 78 completely seals the path to the oropharyngeal cavity 88.

If blowing respiratory air through the mouthpiece 44 is stopped, the soft palate 76 opens up the path from the nasal cavity 80 into the oropharyngeal cavity 88 but the valve 32 closes, as a result of which the outflow of further irrigation liquid 14 is interrupted.

At this point, it should be mentioned that the cap part 24 is formed anatomically in such a way that the nasal douche 10 can be held by one hand and it is positionable at the first nostril 70 in such a way that premature leakage of the irrigation liquid 14 from the container part 12 is precluded as a result of the hydrostatic pressure on the irrigation liquid 14 and the valve member 36.

Figure 3:
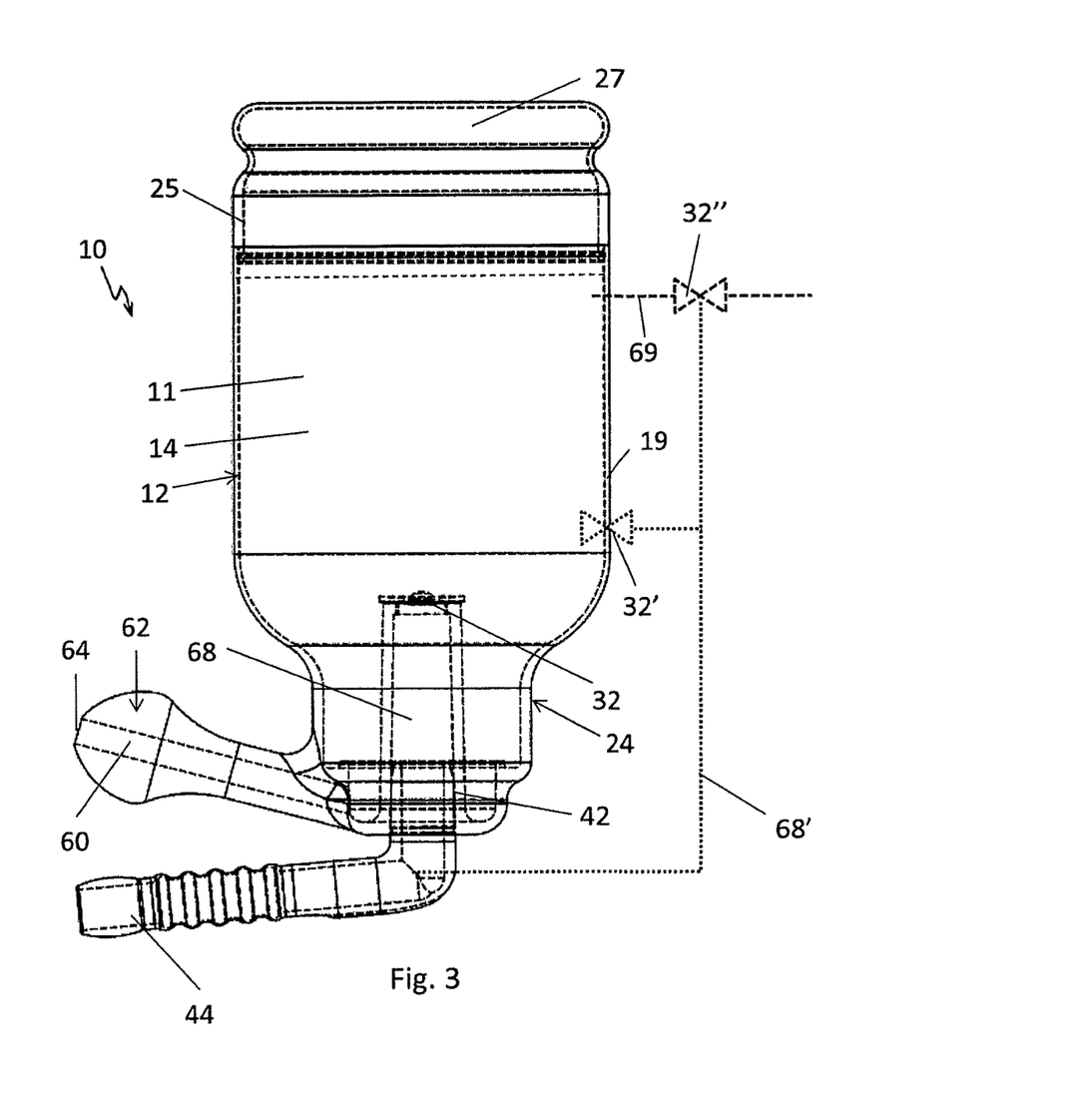
FIG. 3 shows a longitudinal section of a nasal douche according to the invention, comprising a container part and a cap part, which together have an integral embodiment, wherein the container part serves to receive irrigation liquid and the cap part is provided with a nose attachment and an assigned mouthpiece, as well as a valve such that the valve, in the rest position, prevents the drainage of irrigation liquid through the mouthpiece.

In a further exemplary embodiment of the present invention in accordance with FIG. 3, the container part 12 is embodied in an integral manner with the cap part 24. Use is made of the same reference signs as in conjunction with FIG. 1 and FIG. 2.

Since the container part 12 and the cap part 24 together have an integral embodiment, a refill opening 25 is provided in the container part 12 for filling the container part 12 with irrigation fluid 14, said refill opening being sealable by means of a lid 27.

The valve 32 is assigned to the cap part 24 in the same way and the mouthpiece 44 is also inserted in the same way into the receptacle 42 of the cap part 24 as was explained in detail in conjunction with FIG. 1.

Accordingly, the functional effect in the exemplary embodiment in accordance with FIG. 3 is identical to that as was explained in detail in conjunction with FIG. 2.

Consequently, the valve 32 is closed in the rest position such that the drainage of irrigation liquid 14 from the container part 12 in the direction of the outlet opening 64 is precluded and the valve 32 can be brought into the open position by actuation with respiratory air by virtue of the user blowing respiratory air into the mouthpiece 44 such that, in the open position of the valve 32, respiratory air reaches the container part 12, as a result of which the drainage of irrigation liquid 14 from the container part 12 in the direction of the outlet opening 64 is enabled.

Alternatively, it should be mentioned at this point that the mouthpiece 44 is also directly connectable to a valve 32' attached to an outer wall 19 of the container part 12 by way of a tube connection 68' (depicted by dotted lines), as indicated by dotted lines in FIG. 3. Here, the valve 32' is inserted into an opening in the outer wall 19 of the container part 12 with the same functional effect as described in detail in conjunction with FIG. 2. It should be mentioned, in particular, that respiratory air from the mouthpiece 44 likewise reaches the container part 12 when the valve 32' is in the open position and the drainage of irrigation liquid 14 from the container part 12 in the direction of the outlet opening 64 is thus enabled.

Moreover, it is also possible for the valve 32", as likewise drawn with dotted lines in FIG. 3, to be situated in an inlet channel 69, wherein the valve 32" precludes the access of ambient air into the interior 11 of the container part 12 in the rest position and wherein said valve can be brought into the open position when the valve 32" is actuated by respiratory air by virtue of the user blowing respiratory air into the mouthpiece 44 such that, in the open position of the valve 32", ambient air reaches the container part 12, as a result of which the drainage of irrigation liquid 14 from the container part 12 in the direction of the outlet opening 64 is enabled.

Figure 4:
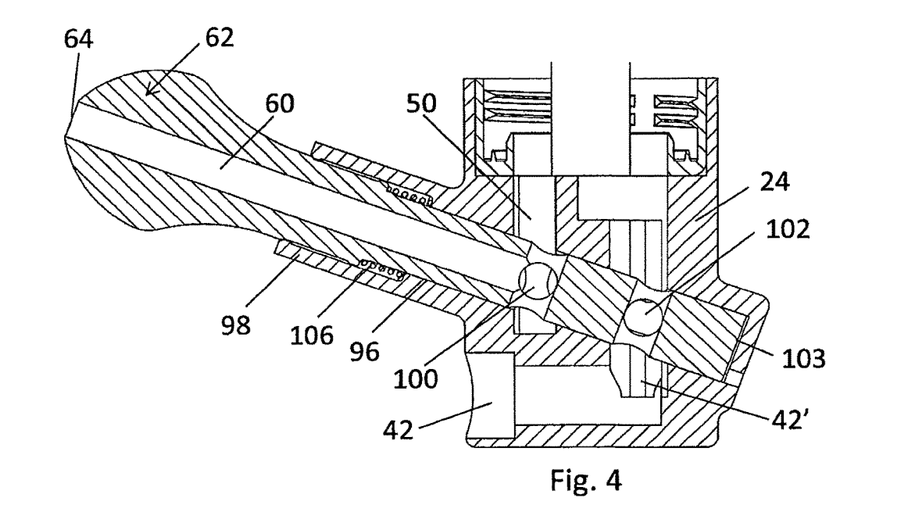
FIG. 4 shows a longitudinal section through a nose attachment in the open position, wherein the nose attachment is retracted in a blind hole-shaped receptacle in the longitudinal direction.
Figure 5:
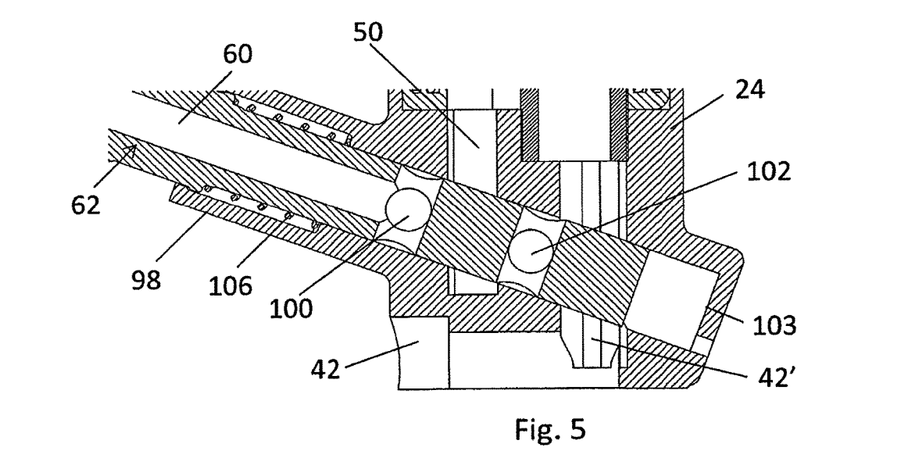
FIG. 5 shows a longitudinal section through the nose attachment in the rest position, wherein the nose attachment is extended in the blind hole-shaped receptacle in the longitudinal direction.

In the embodiment in accordance with FIGS. 4 and 5, the nose attachment 62 does not have an integral embodiment with the cap part 24, but rather it is a separate, straight part which is mounted in a blind hole-shaped receptacle 96 in a manner displaceable along the longitudinal direction thereof. The receptacle 96 is formed by the cap part 24 and an appendage 98 integrally formed thereon.

The appendage 98 is angled in a direction against the bottle base 16.

In the nose attachment 62, the discharge channel 60 has a blind hole-like embodiment, wherein, on the inside at the closed end of the discharge channel 60, transversely radial first apertures 100 are connected by the nose attachment 62 to the discharge channel 60.

Transversely radial second apertures 102 are removed from the nose attachment 62, said second apertures being separate from the discharge channel 60.

A spring 106 acting between the appendage 98 and the nose attachment 62 pushes the nose attachment 62 into an (extended) rest position shown in FIG. 5, in which the first and second apertures 100, 102 are sealed by the cap part 24.

At the same time, the nose attachment 62 seals a connection channel 42' between the receptacle 42 of the cap part 24 for the mouthpiece 44 and the container part 12.

For the purposes of irrigating the nasal cavity 80, the nose attachment 62 is placed against the one nostril 70 and, by pressing the cap part 24 in the direction against the nose, the nose attachment 62 is inserted inward in the direction of the cap part 24 against the force of the spring 106 until the nose attachment 62 rests against the base 103 of the receptacle 96, as shown in FIG. 4.

From the surroundings, a supply hole guides the cap part 24 to the base 103 of the receptacle 96.

In the work or irrigation position shown in FIG. 4, the second apertures 102 on the one hand open up the connection channel 42' and, on the other hand, the flow connection between the passage 50 and the discharge channel 60 is established for the first apertures 100.

If respiratory air is blown into the container part 12 through the mouthpiece (not depicted here) inserted into the receptacle 42, irrigation liquid 14 emerges through the first apertures 100 and the discharge channel 60 and thus reaches the nose of the user.

If the cap part 24 is moved away from the nose, the nose attachment 62 acting as a double valve member moves back into the rest position under the force of the spring 106.

Figure 6:
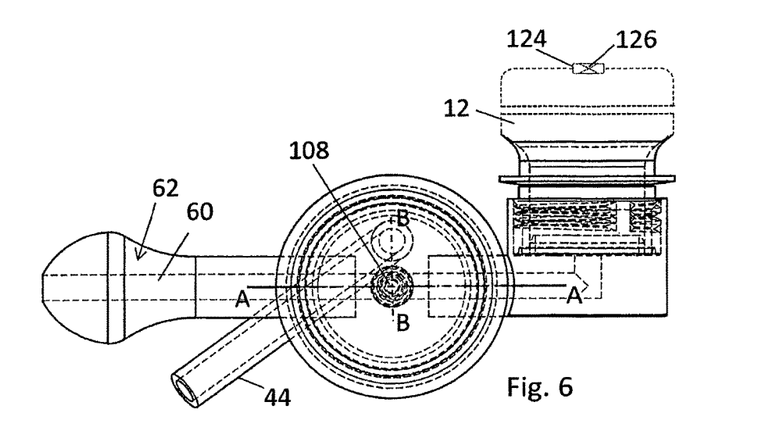
FIG. 6 shows a top view of an embodiment, in which a valve seals a discharge channel in the nose attachment.
Figure 7:
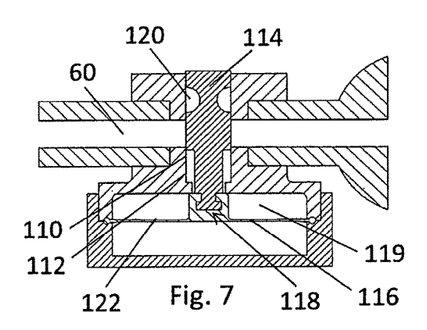
FIG. 7 shows a longitudinal section through the discharge channel along the line A-A in accordance with FIG. 6 in a rest position.

FIG. 6 in conjunction with FIG. 7 shows a further embodiment of the present invention, in which the valve 108 seals the discharge channel 60 in the nose attachment 62 and opens this up when actuated by respiratory air.

The nose attachment 62 has a passage 110 across the discharge channel 60 as a valve seat 112. The valve seat 112 interacts with a valve member 118, which is embodied as a closure pin 114 and interacts with an actuation organ 116.

In the rest position in accordance with FIG. 6, the closure pin 114 seals the discharge channel 60.

Figure 8:
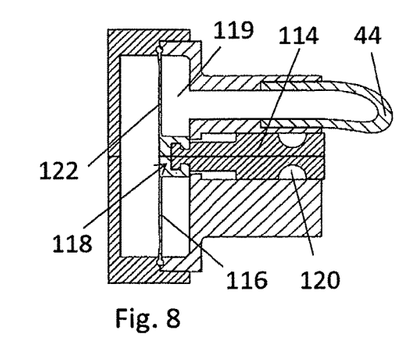
FIG. 8 shows a longitudinal section through an attachment of a mouthpiece and an actuation organ for a valve along the line B-B in accordance with FIG. 6 in a rest position.
Figure 9:
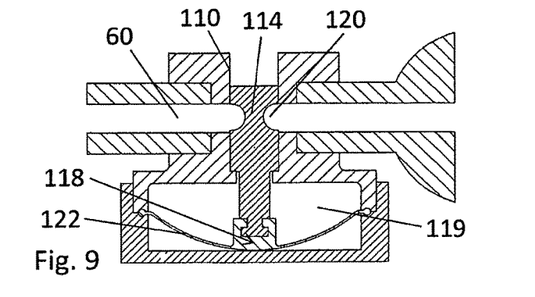
FIG. 9 shows a longitudinal section through the discharge channel in accordance with FIG. 6 when pressure is applied by respiratory air from the mouthpiece in an open position.

When actuating a blowing-in cavity 119 between the actuation organ 116 and the mouthpiece 44 with respiratory air from the mouthpiece 44, as shown in FIG. 8 in conjunction with FIG. 9, the actuation organ 116 displaces the closure pin 114 in such a way that an aperture 120 in the form of a circumferential groove in the closure pin 114 opens up the discharge channel 60.

The actuation organ 116 preferably has a rubber-elastic membrane 122 which, depending on the respiratory air in the blowing-in cavity 119, can expand as shown in FIG. 9 or retract again as shown in FIG. 7 in order to accordingly move the closure pin 114 back and forth in the passage 110.

Preferably, a connection channel (not shown here) with a preferably smaller cross section than the discharge channel 60 leads from the blowing-in cavity 119 to the interior 11 of the container part 12, in order to guide the respiratory air from the mouthpiece 44 into the container part 12 in the open position of the valve 108.

However, it is also conceivable for the container part 12 to have a ventilation opening 124 and be provided with a check valve 126 instead of the connection channel, said check valve preventing the emergence of irrigation liquid 14 from the container part 12 through the ventilation opening 124 and admitting the inflow of ambient air through the ventilation opening 124 into the container part 12 such that, in the open position of the valve 108, the ambient air flowing into the container part 12 enables the drainage of the irrigation liquid 14 in the direction of the discharge channel 60.

The invention claimed is:

1. A nasal douche comprising:
   a container part and a cap part, an interior of the container part receiving irrigation liquid, the container part carrying the cap part;
   a nose attachment of the cap part having an outlet opening for the irrigation liquid, the outlet opening being flow-connected to the interior of the container part via a discharge channel, the nose attachment being configured to attach to a nostril of a user;
   a valve closed in a rest position preventing the drainage of irrigation liquid through the nose attachment; and
   a mouthpiece controlling the valve, the mouthpiece being associated with the container part or the cap part, wherein
   the valve is moved to an open position by actuation with respiratory air when the user blows respiratory air into the mouthpiece and irrigation liquid flows out through the nose attachment as a result of the blown respiratory air into the mouthpiece, with respiratory air or ambient air flowing into the interior of the container part for drainage.

2. The nasal douche as claimed in claim 1, wherein the container part is embodied as an independent component and the cap part is embodied as an independent component, and the container part and the cap part are fastened to one another.

3. The nasal douche as claimed in claim 2, wherein the cap part and the container part are fastened to one another by means of a screw-in connection or a bayonet closure.

4. The nasal douche as claimed in claim 2, wherein the cap part and the container part are fastened to one another by means of a force fit.

5. The nasal douche as claimed in claim 1, wherein the container part has an integral embodiment with the cap part.

6. The nasal douche as claimed in claim 5, wherein the container part has a refill opening, which is sealable by means of a lid.

7. The nasal douche as claimed in claim 1, wherein the valve, in the rest position, seals a blown-in air channel leading from the mouthpiece to the container part, as a result of which no respiratory air or ambient air reaches the container part and the drainage of irrigation liquid from the container part in a direction of the outlet opening is prevented, and the valve is moved to the open position when actuated with respiratory air such that the respiratory air reaches the container part via the blown-in air channel or ambient air reaches the container part and the irrigation liquid drains from the container part in the direction of the outlet opening.

8. The nasal douche as claimed in claim 1, wherein the valve has a valve seat that is ring-shaped and formed on the cap part, and a plate-shaped valve member that is located to intersect between the valve seat and the cap part.

9. A nasal douche comprising:
   a container part and a cap part, an interior of the container part receiving irrigation liquid, the container part carrying the cap part;
   a nose attachment of the cap part having an outlet opening for the irrigation liquid, the outlet opening being flow-connected to the interior of the container part via a discharge channel, the nose attachment being configured to attach to a nostril of a user;

a valve including a valve seat, the valve being closed in a rest position preventing the drainage of irrigation liquid through the nose attachment;

a mouthpiece controlling the valve, the mouthpiece being associated with the container part or the cap part; and a web with a head, wherein:

the valve member abuts on the valve seat and is embodied in a membrane-like, elastically deformable manner, the valve member having a through hole at a central location, and that is pulled over the head with the through hole during assembly and engages behind the head in the assembled state; and the valve is moved to an open position by actuation with respiratory air when the user blows respiratory air into the mouthpiece and irrigation liquid flows out through the nose attachment as a result of the blown respiratory air into the mouthpiece, with respiratory air or ambient air flowing into the interior of the container part for drainage.

10. The nasal douche as claimed in claim 1, wherein the mouthpiece arranged at the cap part has an elastic material such that different distances between mouth and nose of the user are compensable during application.

11. The nasal douche as claimed in claim 1, wherein the mouthpiece is interchangeable.

12. The nasal douche as claimed in claim 1, wherein the mouthpiece is insertable in an interchangeable manner into a receptacle of the cap part or pluggable onto an attachment of the cap part, the mouthpiece having a straight or angled embodiment.

13. The nasal douche as claimed in claim 1, wherein the valve seals the discharge channel in the rest position and opens up the discharge channel in the open position.

14. A nasal douche comprising:

a container part and a cap part, an interior of the container part receiving irrigation liquid, the container part carrying the cap part;

a nose attachment of the cap part having an outlet opening for the irrigation liquid, the outlet opening being flow-connected to the interior of the container part via a discharge channel, the nose attachment being configured to attach to a nostril of a user;

a valve closed in a rest position preventing the drainage of irrigation liquid through the nose attachment;

a mouthpiece controlling the valve, the mouthpiece being associated with the container part or the cap part, wherein:

the valve is moved to an open position by actuation with respiratory air when the user blows respiratory air into the mouthpiece and irrigation liquid flows out through the nose attachment as a result of the blown respiratory air into the mouthpiece, with respiratory air or ambient air flowing into the interior of the container part for drainage;

the valve seals the discharge channel in the rest position and opens up the discharge channel in the open position; and the valve has a passage across the discharge channel as a valve seat, which interacts with a valve member, which is embodied as a closure pin and interacts with an actuation organ, in such a way that the closure pin seals the discharge channel in the rest position and the actuation organ displaces the closure pin in the open position when actuated by respiratory air in such a way that an aperture opens up the discharge channel.

15. A nasal douche comprising:

a container part and a cap part, an interior of the container part receiving irrigation liquid, the container part carrying the cap part;

a nose attachment of the cap part having an outlet opening for the irrigation liquid, the outlet opening being flow-connected to the interior of the container part via a discharge channel, the nose attachment being configured to attach to a nostril of a user;

a valve closed in a rest position preventing the drainage of irrigation liquid through the nose attachment;

a mouthpiece controlling the valve, the mouthpiece being associated with the container part or the cap part, wherein:

the valve is moved to an open position by actuation with respiratory air when the user blows respiratory air into the mouthpiece and irrigation liquid flows out through the nose attachment as a result of the blown respiratory air into the mouthpiece, with respiratory air or ambient air flowing into the interior of the container part for drainage;

the valve seals the discharge channel in the rest position and opens up the discharge channel in the open position; and the container part has a ventilation opening and is provided with a check valve which prevents emergence of irrigation liquid from the container part through the ventilation opening and admits inflow of ambient air through the ventilation opening into the container part.

* * * * *